(12) United States Patent
Bissinger et al.

(10) Patent No.: US 7,700,666 B2
(45) Date of Patent: Apr. 20, 2010

(54) COMPOSITION CONTAINING A PREPOLYMER AND A CROSSLINKER, PROCESS FOR PRODUCING AND USE THEREOF

(75) Inventors: Peter Bissinger, Diessen (DE); Thomas Klettke, Diessen (DE)

(73) Assignee: 3M ESPE AG, Seefeld (DE)

( * ) Notice: Subject to any disclaimer, the term of this patent is extended or adjusted under 35 U.S.C. 154(b) by 811 days.

(21) Appl. No.: 11/423,021

(22) Filed: Jun. 8, 2006

(65) Prior Publication Data
US 2006/0281829 A1    Dec. 14, 2006

(30) Foreign Application Priority Data
Jun. 10, 2005    (EP) .................................. 05012474

(51) Int. Cl.
A61K 6/10    (2006.01)
C08G 73/06    (2006.01)
A61C 9/00    (2006.01)
(52) U.S. Cl. ........................ 523/109; 528/423; 433/214
(58) Field of Classification Search ................ 523/109; 528/423
See application file for complete search history.

(56) References Cited

U.S. PATENT DOCUMENTS

| | | | |
|---|---|---|---|
| 3,453,242 A | 7/1969 | Schmitt et al. | |
| 3,453,742 A | 7/1969 | Diederen | |
| 3,541,068 A | 11/1970 | Taylor | |
| 3,956,216 A * | 5/1976 | Tucker | 524/809 |
| 4,709,741 A | 12/1987 | Nakamura | |
| 5,286,105 A | 2/1994 | Herold | |
| 5,569,691 A | 10/1996 | Guggenberger et al. | |
| 6,037,444 A | 3/2000 | Rannard et al. | |
| 6,127,449 A | 10/2000 | Bissinger et al. | |
| 6,218,461 B1 | 4/2001 | Schwabe et al. | |
| 6,833,425 B1 | 12/2004 | Hecht et al. | |
| 6,894,144 B1 | 5/2005 | Zech et al. | |
| 2003/0153726 A1 | 8/2003 | Eckhardt et al. | |
| 2004/0146713 A1 | 7/2004 | Schaub et al. | |
| 2004/0149164 A1 | 8/2004 | Eckhardt et al. | |

FOREIGN PATENT DOCUMENTS

| | | |
|---|---|---|
| DE | 4321257 A1 | 8/1996 |
| EP | 1210055 B1 | 6/2002 |
| JP | 62-057415 | 12/1987 |
| WO | WO 00/13677 | 3/2000 |
| WO | WO 01/17483 | 3/2001 |
| WO | WO 01/45796 A2 | 6/2001 |
| WO | WO 01/45796 A3 | 6/2001 |

OTHER PUBLICATIONS

DIN 53504, 1994.
DIN 53505, 2000.
DIN EN ISO 4823:2000.

E. Ranucci, P. Ferruti, Synth. A New Synthetic Method for Amino-Terminated Poly0(Ethyleneglycol) Derivatives Comm. 20 (1990) 2951-2957.
Encyclopedia of Polymer Sciences and Engeneering (Ed. H. Mark et al) vol. 1, Chapter: Alkyl-enelimine Polymers, pp. 688-695, A Wiley-Interscience Publication, New York, 1985.
H.A. Staab, H. Bauer, K.M. Schneider "Azolides in organic synthesis and biochemistry", Wiley-VCH, 1998, Chap 1, 1-12.
L. Cotarca, H. Eckert "Phosgenations—A Handbook", p. 46-72 and 149-170, Wiley-VCH 2003.
Neue Methoden der präparativen Organischen Chemie, Band V, W. Foerst (Ed.) S. 53-93, Verlag Chemie 1967/Staab, et al. Syntheses Using Heterocyclic Amides (Azolides).
S.P. Rannard, Controlled Synthesis of Asymmetric Dialkyl and Cyclic Carbonates Using the Highly Selective Reactions of Imidazole Carboxylic Esters, N.J. Davis Org. Lett. 1 (1999) 933-936.
Ullmanns Enzyklopädie der technischen Chemie, 4. Auflage, Verlag Chemie, Weinheim, Band 24, p. 3, 1983.
Vinogradov, S.; Batrakova, E.; Kabanov, A: "Nanogel™ particles: Novel drug delivery systems for antisense oligonucleotides" Colloids and Surfaces B: Biointerfaces, vol. 16, No. 1-4, 1999, p. 291-304, XP002353327 netherlands—abstract.
Rannard, et al, A Highly Selective, One-Pot Multiple-Addition Convergent Synthesis of Polycarbonate Dendrimers, J.Am.Chem.Soc. 2000,122,11729-11730.

* cited by examiner

Primary Examiner—Tae H Yoon
(74) Attorney, Agent, or Firm—Pamela L. Stewart; Ann M. Mueting

(57) ABSTRACT

The invention relates to a curable composition comprising prepolymer (A) having the formula:

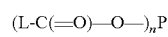

wherein
L is a group represented by the following formula

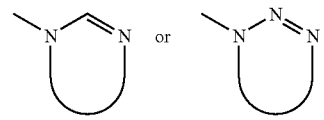

with the N,N' bridging unit being part of a heterocyclic quasi-aromatic ringsystem, optionally containing O, N or S, preferably an azolide,
P is a prepolymer backbone having a molecular weight (Mn) of at least 500,
n is at least 2,
and crosslinker (B) comprising at least 3 nucleophilic groups.

The curable composition can be used for coating, sealing, moulding, adhering, making impressions, especially in the dental field.

32 Claims, No Drawings

COMPOSITION CONTAINING A PREPOLYMER AND A CROSSLINKER, PROCESS FOR PRODUCING AND USE THEREOF

CROSS REFERENCE TO RELATED APPLICATION

This application claims priority from European Serial No. 05012474.2, filed on Jun. 10, 2005.

The invention relates to a curable composition comprising a prepolymer and a crosslinker containing nucleophilic groups. Those compositions can be used broadly for coating, sealing, moulding, adhering, making impressions, especially but not limited to the dental field. The invention also relates to a process for producing a curable composition and processes for using the curable composition provided.

JP 62-057415 describes the synthesis of a blocked isocyanate compound obtained by reacting (A) an urethane polymer containing liberated NCO groups in the molecule with (B) a heterocyclic compound (e.g., imidazole, etc.). Then, the blocked isocyanate compound is blended with a mixture comprising polyglycerin or an esterified substance of it and an organic carboxylic acid, (D) nitrogen atom-containing polymer, (E) inorganic filler, (F) electrolytic salt and (G) water, to give a composition. It is stated that the composition is suitable as a dental impression material.

U.S. Pat. No. 3,453,242 describes certain curable elastomers derived from polyethers and ethylene imine compounds. The elastomers are substantially linear in structure and contain ethylene imine groups, in particular at the ends of the chains. The patent states that these materials can be cured to obtain rubber-like products using acidic starters. These materials are commercially available and are relatively expensive in comparison to materials described e.g. in U.S. Pat. No. 6,218,461 B1 or US 2004/0146713. The materials described in the latter references have a polyether containing backbone with silicone side chains and cure through condensation reaction.

Silicone-based compositions curable by condensation reactions (i.e. "C-silicones") are often low cost, but many have poor dimensional stability in comparison to dental impression materials containing silicones or polyethers curing by addition reactions. One cause of the poor dimensional stability of C-silicones is thought to be caused by migration of the low molecular condensation (mostly alcohols or acetic acid) by-products out of the mould of the impression tray.

The market for dental impression materials based on addition curing silicones (i.e., "A-silicones") has grown at the expense of alginate dental impression materials and C-silicone impression materials. However, these materials are more expensive and their cost impacts market growth.

Moreover, both classes of materials (C-silicones and A-silicones) lack the initial hydrophilicity inherent to polyether materials.

Thus, there is a need for a storage stable composition, which can be manufactured in an easy and cheap manner.

It would be an advantage, if the composition shows comparably good physical properties, like sufficient elongation at break.

In addition, it would be an advantage, if the curing reaction could be initiated without a molecular organometallic or acidic initiator. The acidic initiator has to be handled with care when it is not neutralized with a basic compound. The absence of organometallic initiators can also be desirable in applications where organometallic compounds may decompose over time to reduce shelf life stability.

Moreover, it would be an advantage, if water did not have to be added to the composition thus reducing any potential for altered cure or rheological properties due to evaporation of the water.

The invention provides a composition containing a prepolymer and a crosslinker containing nucleophilic groups as described in the claims and text below. The invention also provides a process for producing a curable composition and processes for using it.

In one aspect, the invention provides a curable composition comprising prepolymer (A) having the formula:

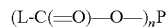

wherein

L is a group represented by the following formula

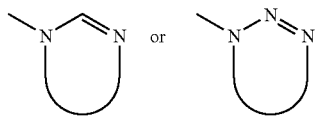

with the N,N' bridging unit being part of a heterocyclic quasi-aromatic ringsystem, optionally containing O, N or S, preferably an azolide, P is a prepolymer backbone having a molecular weight (Mn) of at least 500, n is at least 2, and crosslinker (B) comprising at least 3 nucleophilic groups.

Index n can be at least 2, 3, 4, 5, 6, 7 or 8 and can be in a range of at least 2 to about 1000 or at least 2 to about 100, or at least 2 to about 20, or at least 2 to about 10.

The quasi-aromatic ringsytem can comprise a pentamerous ring structure, optionally connected with a substituted or unsubstituted aryl ring. This structural unit can be named as azolide.

Azolides are heterocyclic amides in which the amide nitrogen is part of an azole ring, such as imidazole, pyrazole triazole, tetrazole, bezimidazole, benzotriazole, and their substituted derivatives (c.f. H. A. Staab, H. Bauer, K. M. Schneider "Azolides in organic synthesis and biochemistry", Wiley-VCH, 1998 [ISBN: 3-527-29314-0] page. 1). In the context of the invention amides are understood as derivatives of carbonic acid, especially urethanes.

Examples for group L are substituted or unsubstituted imidazole, triazole, pyrazole triazole, tetrazole, benzimidazole or benzotriazole. Possible substitutions can be $C_1$ to $C_6$ alkyl groups or aryl groups.

In another aspect, the invention provides a process for producing the curable composition described above as well as a dental material comprising the curable composition and its use for coating, sealing, moulding, adhering or making impressions.

It was found that the composition can be manufactured in an easy and cheap manner. The curing reaction can be initiated without a molecular organometallic or acidic initiator. Generally speaking, the addition of acidic initiators as described e.g. in DE 43 21 257 A1, EP 1 210 055 A1 or US 2003/153726 A1 for N-alkyl aziridino polyether formulations is not mandatory for initiating the curing reaction.

If the prepolymer backbone is derived from or contains e.g. polyol containing structures, the composition is sufficiently hydrophilic that it can be used in applications where hydrophilicity is needed or is desirable, such as in dental impressioning.

The terms "comprise" and "contain" within the meaning of the invention introduce a non exhaustive list of features. Likewise, the word "one" or "a" is to be understood in the sense of "at least one".

The term "crosslinker" refers to compounds that are able to react with the functional group or groups on the polymer chains to lengthen them and/or connect them, e.g., to form a crosslinked network like that of a cured elastomer. In contrast to a thermoplastic polymer, (i.e., a polymer that softens and flows upon heating) a crosslinked polymer, after crosslinking, is usually incapable of further flow. Cross-linked polymers differ in some important respects from linear and branched polymers. For example they swell in suitable solvents to form a gel but they can not be dissolved to form a solution. At elevated temperature, cross-linked polymers behave like soft but elastic solids rather than viscous liquids. An effective crosslinker usually comprises more than one reactive site. These reactive sites are capable to undergo a chemical reaction with the prepolymer of the invention.

The term "dental materials" comprises impression materials, such as precision impression materials, situation impression materials, bite registration materials, duplicating materials (applicable for the duplication of master models, e.g. for all-ceramic restorations requiring a refractory investment model and when inlays, onlays, cantilevers and other precision attachments are being fabricated) and modelling materials (applicable for e.g. reconstructing the gingival, producing crowns and bridges). Duplicating and modelling materials are commercially available e.g. from 3M ESPE AG under the trademarks Reprogum™ or Vestogum™.

The example prepolymers useful in the invention may be block, multi block, random, gradient, alternating co- and ter polymers, and may have linear, branched, hyperbranched or dendrimeric structures.

The terms "block", "multi block", "random", "gradient", "linear", "branched", "hyperbranched" or "dendrimeric" are know to the skilled person in the art. Respective definitions of these terms can be found e.g. in Encylopedia of Polymer Science and Technology, John Wiley & Sons. Inc.

Representative examples of the prepolymers include those having groups L, that are substituted or unsubstituted imidazole, benzimidazole, benzotriazole or triazole containing groups. Such substituents can include, for example, $C_1$ to $C_6$ alkyl or aryl groups.

Representative values for the molecular weight (Mn) of the prepolymer can be in a range of about 500 gmole$^{-1}$ to about 50,000 gmole$^{-1}$, or in a range of about 1,000 gmole$^{-1}$ to about 30,000 gmole$^{-1}$ or in a range of about 2,000 gmole$^{-1}$ to about 20,000 gmole$^{-1}$. The molecular weight can be determined, for example by GPC for the higher molecular weight materials and by end group titration for the lower molecular weight materials.

Typically, the prepolymer will have sufficient viscosity to insure adequate mixing with other components needed to prepare a curable composition. Typical prepolymers will have viscosities in the range of about 0.01 Pa*s to about 1000 Pa*s, or preferably, in the range of about 0.1 Pa*s to about 500 Pa*s, or more preferably in the range of about 0.5 Pa*s to about 250 Pa*s, at 23° C.

Generally, up to about 10 wt.-% of the prepolymer can be composed of materials that are waxy or solid at 23° C.

The prepolymer backbone P may be derived from organic polymeric polyols, e.g., organic polymeric diols and triols, such as, for example, polyethylene glycol (such as CAS 25322-68-3)

polypropylene glycol, diol or triol (such as CAS 25322-69-4)

polytetrahydrofuran (such as CAS 25190-06-1)

polycaprolactone diol (such as CAS 36890-68-3, 24980-41-4)

polycaprolactone triol (such as CAS 37625-56-2)

polyglycerol (such as CAS 25618-55-7).

Representative organic polymer polyols suitable for preparing the prepolymer are commercially available, for example, from Aldrich, Sakamoto Yakuhin Kogyo Co., Ltd., Clariant, BASF, ARCO Chemical Company or can be synthesized as described by Aldrich, Gelest, TEGO, Rhone-Poulenc). Block polymeric-, multi-block polymeric, random polymeric, gradient polymeric- and alternating co- and terpolymeric forms of these materials are useful in the invention.

Useful prepolymers may also have backbones derived from monomers containing silicone groups and/or monomers containing hydroxyalkyl-groups. One type of such materials is the silicone carbinol (such as CAS 156327-07-0, 68937-54-2, 58130-02-2, 102782-61-6, 94469-32-6).

Prepolymers useful in the invention can be prepared by reaction of hydroxy functional polymers and carbonylbisazolides (e.g. 1,1'-carbonyldiimidazole (CDI) CAS [530-62-1], 1, 1'-carbonyldibenzimidazole CAS [14667-54-0], 1, 1'-carbonyldi-(1,2,4)-triazole CAS [41864-22-6], 1, 1'-carbonylbis-(2-methylimidazole) CAS [13551-83-29), 1, 1'-carbonyldibenzotriazole CAS [68985-05-7] or others described in "Neue Methoden der präparativen Organischen Chemie, Band V", W. Foerst (Ed.) S. 53-93, Verlag Chemie 1967. A possible procedure for synthesis of the prepolymers is described in S. P. Rannard, N. J. Davis Org. Lett. 1 (1999) 933-936. Also useful is the process of preparing prepolymeric bis-imidazolides as described in E. Ranucci, P. Ferruti, Synth. Comm. 20 (1990) 2951-2957, starting from low molecular polyethyleneglycols. Another useful process can also be found e.g. in U.S. Pat. No. 3,453,242. Yet another process of preparation is described in L. Cotarca, H. Eckert "Phosgenations—A Handbook", p 46ff and 149ff, Wiley-VCH 2003 (ISBN: 3-527-29823-1), where hydroxy functional compounds are first reacted with phosgene and the chloroformate generated can be converted with an azole base (e.g. imidazole, benzimidazole, triazole, benzotriazole or others) in the presence of excess base to give a prepolymer.

Generally, the prepolymers are relatively stable to moisture and alcohols, but react rapidly with primary amines even at room temperature. Whereas according to U.S. Pat. No. 6,037, 444, the reaction of monomeric carbonyl imidazolides (reaction product of alcohols with carbonyl-diimidazole (CDI) ) with primary amines takes hours at 60° C., surprisingly the reaction of the inventive prepolymers with crosslinkers comprising nucleophilic groups such as e.g. multifunctional amines can take less than an hour at room temperature, in certain cases, can take even less than 10 minutes to obtain tack-free elastomers.

It was found that after an induction period in the range of a few seconds (e.g. up to about 10, 20 or 30 s) to a few minutes (e.g. up to about 1, 2, 3 or 5 min) curing proceeds under ambient conditions (temperature below about 50° C., or below about 30° C., or below about 25° C.) within a few minutes (e.g. about 1, 5, 10, 30 or 60 min) resulting in elastomeric materials.

The curable composition after curing preferably satisfies at least one, preferably two or more, and sometimes all of the following characteristics:

Shore A hardness according to DIN 53505 (measured 24 h after mixing) above about 23 or above about 30 or above about 35. Values up to about 90 up to about 75 or up to about 60 can be reached.

Tensile strength (MPa) according to DIN 53504 geometry S2 above about 0.3 or above about 0.5 or above about 0.8 or above about 1.0. Values up to about 6.0, up to about 5.0 or up to about 4.0 can be reached depending on the chosen reactive components and their amount.

Elongation at break (%) according to DIN 53504 geometry S2 above about 40, or above about 100, or above about 120 or above about 200. Values up to about 1000 can be reached.

The measurements for Shore A hardness, tensile strength, elongation at break are described in the section "test methods" in connection with the examples.

It was found that the cured composition often has improved rubber elastic properties such as good values in regard to elongation at break or dimensional stability.

If hydrophilicity of the composition is important, either prepolymer (A) or crosslinker (B) or prepolymer (A) as well as crosslinker (B) might comprise hydrophilic groups. In this respect, the glycol units containing backbones mentioned above are suitable.

Generally, the curable composition can comprise prepolymer (A) at an amount of about 5 to about 80 wt.-%, or at an amount of about 10 to about 70 wt.-%, or at an amount of about 15 to about 60 wt.-% with respect to the whole composition.

An effective amount of crosslinker (B) should be used to provide the desired level and speed of cure. Typical amounts of crosslinker (B) are about 0.1 to about 20 wt.-% or, of about 0.2 to about 10 wt.-% or of about 0.5 to about 5 wt.-% with respect to the whole composition.

The molecular weight of crosslinker (B) is not limited, however, it is typically selected such that setting with prepolymer (A) will take place under reasonable conditions (e.g. room temperature within a reasonable time frame (e.g. less than one hour)).

Representative values for the molecular weight ($M_n$) of crosslinker (B) can be in a range of about 130 $\text{gmole}^{-1}$ to about 60,000 $\text{gmole}^{-1}$, or in a range of about 200 $\text{gmole}^{-1}$ to about 20.000 $\text{gmole}^{-1}$ or, in a range of about 300 $\text{gmole}^{-1}$ to about 5.000 $\text{gmole}^{-1}$. Depending on the molecular weight, crosslinker (B) can be a substance comprising polymeric molecules having a distribution of molecular weights.

Typically, crosslinker (B) will have a sufficient viscosity to insure adequate mixing with other components needed to prepare a curable composition. Typical viscosities for crosslinker (B) are in a range of about 0.01 Pa*s to about 100 Pa*s, or in a range of about 0.03 Pa*s to about 50 Pa*s, or in a range of about 0.05 Pa*s to about 25 Pa*s.

However, at room temperature (about 23° C.) crosslinker (B) can be partly or entirely solid, if taken alone, under the proviso that the solids are at least partly soluble in the reaction mixture.

The nucleophilic groups of crosslinker (B) usually contain elements like N, O and/or S. Nucleophilic groups containing primary amino groups ($-NH_2$) can be advantageous due to their enhanced nucleophilicity compared to secondary amino groups ($-NH-$). However, secondary amino groups can be present as well.

The nucleophilic groups of crosslinker (B) are capable of reacting with the reactive groups of prepolymer (A). Without wishing to be bound to a particular mechanism, it is assumed that during the cure of the curable composition, group L of prepolymer (A) is substituted by one of the nucleophilic groups of crosslinker (B), where the nucleophilic group of crosslinker (B) is more nucleophilic than group L of prepolymer (A) setting free low molecular weight by-product L-H. Thus, the nucleophilic groups of crosslinker (B) should be able to react with group(s) L of the prepolymer (A) forming a network and leading to a cured product.

The low molecular weight by-product L-H is usually an aromatic compound. The molecular weight of the by-product can be within a range of about 65 $\text{gmol}^{-1}$ to about 200 $\text{gmol}^{-1}$ or in a range of about 75 $\text{gmol}^{-1}$ to about 150 $\text{gmol}^{-1}$.

The by-product produced usually have higher boiling points and can even be solid substances at ambient conditions. The boiling point of the by-product produced can be within the range of about 200° C. to about 400° C. or within the range of about 250° C. to about 400° C. Examples for these by-products are e.g. imidazole or benzimidazole. Both are crystalline substances with boiling points above 250° C.

In contrast to the low molecular weight alcohols evaporating from C-Silicones during the setting reaction (e.g. ethanol with a boiling point of 78° C.), the by-products according to the invention will usually have a significantly lower tendency to migrate out of the mould. This can lead to an improved dimensional stability. In contrast to this, evaporating substances might lead to a reduced dimensional stability caused by volume shrinkage of the curing or cured composition.

Speed and quality of network formation and density of the cured or curable composition can be adjusted over a wide range through selection of the quantity of nucleophilic groups being present in the crosslinker, the nature of the nucleophilic groups (e.g. containing N, O and/or S) and the nature of prepolymer backbones chosen (e.g. branched or dendrimeric). For example, if crosslinker (B) is a branched polyethyleneimine, it is likely that the network density is increased compared to an identical composition containing a linear, polyethyleneimine crosslinker (B) because the former material provides a higher net point connectivity than the later.

Also the availability and number of primary and secondary amine groups present in crosslinker (B), as well as their different reactivity towards group L might have an impact on the reaction. It can be assumed that e.g., polyallyl amine or polyvinyl amine with only primary amine groups will behave differently compared to linear polyethyleneimine with mainly secondary amine groups.

The nucleophilic groups may be end groups on a linear or branched backbone, however, they may also be side groups attached to the backbone. In some cases, they even might be part of the backbone. Respective examples are given below.

Preferably, and to enhance crosslinking in the curable composition, crosslinker (B) comprises more than three nucleophilic groups, while prepolymer (A) may comprise only two groups L or, optionally, more than two groups L. Having nucleophilic groups of different reactivities within a particular crosslinker (B) may advantageously impact the desired setting properties of the curable composition.

Crosslinker (B) can comprise at least 3, 4, 5, 6, 7 or at least 8 nucleophilic groups. The overall number of nucleophilic groups comprised by crosslinker (B) is not limited. The number can be as high as about 500 or as high as about 100. Good results can be achieved with crosslinkers comprising nucleophilic groups in a quantity of at least 3 to about 50 or, about 4 to about 20.

Representative examples of crosslinkers (B) include:

Polyethylene imine CAS-No. [25987-06-8] (branched, e.g. prepared from aziridine) $M_n$: 400-75,000, preferably 400-2,000;

Polyethylene imine CAS-No. [29320-38-5] (linear, e.g. prepared from oxazolidine) $M_n$: 300-75,000, preferably 300-2,000;

Polyallylamine CAS-No. [30551-89-4] $M_n$: 300-100,000, preferably 300-30,000;

Tris-aminoethyl-amine CAS-No. [4097-89-6], DAB-AM-4 (Polypropylenimin-tetramin Dendrimer, Generation 1) CAS-No. [120239-63-6] and higher;

Polyamidoamine (PAMAM) available form Dendritic NanoTechnologies Inc. (Starburst™) Dendrimer Generation 1 and higher and Polyglucosamine like Chitosan CAS-No. [9012-76-4].

The curable composition of the invention may also comprise optional filler(s) (C) and optional additive(s) (D).

Mixtures of different prepolymers (A), crosslinkers (B), optional fillers (C) and optional additives (D) can be used as well.

A wide variety of inorganic, especially hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4 to 6 µm); amorphous silicone dioxides, such as a diatomaceous earth (4 to 7 µm); and silanated fumed silica, such as Cab-o-Sil TS-530 (160-240 $m^2/g$), manufactured by Cabot Corporation. Varying the sizes and surface areas of the foregoing materials enables one to control the viscosity and thixotropicity of the uncured as well as the physical properties of the cured compositions. Some or all of the foregoing hydrophobic fillers may be surface treated with one or more silanating agents, as known to those of ordinary skill in the art. Such silanating may be accomplished, e.g., using known halogenated silanes or silazides. Some useful functionalized silicas are commercially available, e.g. products sold under the brands Aerosil™ (Degussa) or HDKH™ (Wacker).

Among the fillers which can be used are non-reinforcing fillers such as quartz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, glass and plastic powder. The non-reinforcing fillers can be surface treated. The surface treatment can generally be carried out with the same methods as described for the reinforcing fillers.

Suitable fillers also include reinforcing fillers such as e.g. pyrogenic or precipitated silicic acid and silica aluminium mixed oxides. The above mentioned fillers can be hydrophobized, e.g. by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than 50 µm.

A combination of reinforcing and non-reinforcing fillers can be desirable. In this respect, the quantity of reinforcing fillers may range from about 0.1 to about 15 wt.-%, in particular from about 1 to about 10 wt.-%. The difference in the named overall ranges, i.e. about 9 to about 80 wt.-%, can be accounted for by non-reinforcing fillers.

As filler (C) is an optional component, it may not be present at all, but typically it will be present in the curable composition at an amount of from about 0 to about 80 wt.-%, or about 5 to about 70 wt.-%, or about 10 to about 60 wt.-% of the total composition.

Besides filler (C) additives (D) can be present like network modifiers, dyes, pigments, thixotropic agents, flow improvers, polymeric thickeners, surfactants, odorous substances, diluters and/or flavourings. All kinds of known and compatible softeners and rheology modifiers like non reactive polymeric fluids or fats commonly used in commercialized impression materials can be added as well as pigments and stabilizers of any kind.

Preferred are those ingredients and additives that do not add unpleasant smell or taste. Compounds that have an unpleasant smell might be removed by thinfilm evaporation, if needed.

Network modifiers contain either one or two nucleophilic groups, capable to react with group L of prepolymer (A). Network modifiers are usually not able to act in the sense of a crosslinker due to the limited number of nucleophilic groups. Mono-functional network modifiers (like e.g. monoamines) function as a stop reagent, di-functional network modifiers (like e.g. diamines) can function as chain extenders.

Suitable thixotropic agent(s) which can be added to the composition of the invention are organic compounds e.g. waxes according to the definition in Ullmanns Enzyklopadie der technischen Chemie, 4. Auflage, Verlag Chemie, Weinheim, Band 24, page 3 or triglycerides as described in U.S. Pat. No. 6,127,449. In general all organic non-water based thixotropic agents are suitable. That means that suitable thixotropic agents can alter the rheology especially of non-water based formulation.

Some of the untreated or surface treated inorganic fillers mentioned above may also contribute to the rheological properties of the formulation. Other thixotropic agents selected from the group of inorganic fillers are modified or unmodified bentonite(s), kaoline(s) and the like.

Suitable surfactant(s) are e.g. polyethers and polyether type materials with special structures such as Pluronic™, Synperonic™, Silwet™ type materials. Especially useful are substances described in U.S. Pat. No. 5,569,691 A1 the disclosure of which especially in regard to surfactants is herewith incorporated by reference.

Suitable diluting agent(s) are liqids that not containing moieties capable of interacting with group L of prepolymer (A). Preferred diluting agents do not contain moieties —SH or —COOH, primary or secondary amino groups, but may contain —OH. Liquids such as $C_{12}$-$C_{15}$ alkyl acetates, liquid derivatives of citric acid, esters of phthalic acid with branched alcohols like bis(2-ethylhexyl)phthalate or polymeric phthalates, $C_2$-$C_{18}$ bis(alkyl)esters of $C_2$-$C_6$ dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene solfonic acid amide, typical aromatic diluters like poly phenyls, dibenzyl toluene, xylyl toluene, dixylyl toluene and polymeric compounds like polyethers, polyesters, polycarbonates, polyolefines can be used. Also low molecular weight alcohols that may contain more than one OH-function like propane-1, 2, diol may be used. From the group of polymeric compounds, polypropylene glycols and its derivatives are preferred.

The additives can be present in amount of about 0 to about 50 wt.-% or in amount of about 1 to about 30 wt.-% or in amount of about 1 to about 20 wt.-% with respect to the whole composition.

Thus, the curable composition can comprise
prepolymer (A) at an amount of about 10 to about 80 wt.-%,
crosslinker (B) at an amount of about 0.1 to about 20 wt.-%,
optional filler (C) at an amount of about 0 to about 80 wt.-%, optional additive (D) at an amount of 0 to about 50 wt.-%.

Curing of the curable composition can be achieved by mixing prepolymer (A) with crosslinker (B) and the other optional components.

If the curing reaction is too slow or the characteristics of the cured product do not satisfy the customers needs, the use of catalysts might be an option. Tin compounds such as dibutyl tin, dioctyl oxide and dibutyltin dilaurate, titanium compounds or zirconium compounds can be used. Respective examples are described e.g. in U.S. Pat. Nos. 6,833,425 B1 and 6,218,461 B1, the disclosure of which especially in regard to procedures useful for producing urethane containing compositions is explicitly mentioned and incorporated herein by reference.

Another option is the addition of (possibly sterically hindered) tertiary amines such as N,N-bis-(hydroxyalkyl)-3,5-xylidines and N,N-bis-(hydroxyalkyl)-3,5-di-t-butylanilines, N,N-bis-([beta]-oxybutyl)-3,5-di-t-butylaniline and N,N-bis-(hydroxyalkyl)-3,4,5-trimethylanilines. Respective examples are described e.g. in U.S. Pat. No. 3,541,068, the disclosure of which especially in regard to tertiary amines is explicitly mentioned and incorporated herein by reference.

However, the addition of organometallic initiators or catalysts is not mandatory.

Dosing of the components can be carried out by sight (e.g., strand-length comparison), by weight, via pre-dosed pack units and subsequent manual mixing, from double-chambered cartridges with static mixing tubes or by means of volume dosing systems with downstream static or dynamic mixers.

An automatic mixing device can be used to mix components (I) and (II) as described in U.S. Pat. No. 5,286,105 A1. Such devices are available on the market as Pentamix™ or Pentamix™ 2 mixing machines. In addition, commercial mixing devices used in dental labs for mixing duplicating materials can be used.

The composition is usually provided as a two-compartment system (kit of parts) in which two pastes are stored separately until mixing. One paste contains prepolymer (A), whereas the other paste contains crosslinker (B). The pastes can be stored e.g. in tubes, cartridges, foil bags or other suitable containers.

The invention also relates to a process for producing a curable composition comprising the steps of providing component (I) comprising prepolymer (A) and component (II) comprising crosslinker (B), mixing component (I) and component (II).

Hereinafter, the mixture can be applied to a surface for curing. In the dental field, the surface can be the surface of soft or hard oral tissue, the surface of a dental impression material, preferably a cured impression material, the surface of a crown or the surface of a model of a tooth stump.

The mixing ratio (volume) of component (I) and component (II) can be in the range of about 0.5:1 to about 15:1 or in the range of about 1:1 to about 10:1. All components (i.e, (I), (II) ) can further comprise filler (C) and/or additive (D).

The curable composition as described above can be used broadly for coating substrates, as sealing material, moulding material, for adhesively fixing substrates and/or making impressions, for modeling of objects or body parts.

The curable composition is especially useful for producing dental materials like precision impression materials, bite registration materials, duplicating materials, modelling materials, situation impression materials.

In this respect, the composition can be used e.g. for making impressions of soft and hard dental tissue. This can simply be achieved, e.g. filling the material into a dental tray and putting the tray into the mouth of a patient.

If used in the dental field, curing is preferably carried out at a temperature below about 50° C. or below about 40° C. or below about 30° C. A useful time range is within about 20 min or within about 10 min after mixing of the components for materials placed in patients mouth and cured (e.g., impression materials) and up to 45 min for materials used in the dental lab (e.g., duplicating materials, modelling materials). In other fields of use (sealing, moulding, coating, adhesively fixing), higher cure temperatures and longer setting times may be employed. Setting times in the range of about 30 min or about 1 hour can still be useful.

The material is regarded as cured, if the cured material fulfils the requirements for its use, e.g. a dental precision impression material typically fulfils the requirements for its use if it fulfils the requirements of ISO 4823:2000 (such as compatibility with gypsum, strain in compression, recovery from deformation, detail reproduction, linear dimensional change).

For dental impression materials two further parameters can be of some importance: working time and oral setting time.

According to DIN EN ISO 4823:2000 impression materials can be classified as Type 0 (kneadable), Type 1 (high viscosity), Type 2 (medium viscosity), and Type 3 (low viscosity).

The total working time at room temperature (23° C.) measured according to DIN EN ISO 4823:2000 for Impregum™ Garant L DuoSoft and Permadyne™ Garant L 2:1 (3M ESPE AG), both Type 3 regular setting polyether precision impression materials, is 3 min 40 s±15 s and 4 min±15 s, respectively.

The oral setting time is given by the manufacturer in the instructions for use. According to DIN EN ISO 4823:2000 the elastomeric property recovery from deformation of the vulcanized material have to reach values of ≧96.5% within the recommended oral setting time. In addition according to DIN EN ISO 4823:2000 the elastomeric property strain in compression of the vulcanized material has to come up to a value within the range of 0.8 to 20.0% for Type 0 and Type 1 materials and in the range of 2.0 to 20.0% for Type 2 and Type 3 materials, respectively within the recommended oral setting time.

If the composition is to be used as dental impression material, appropriate working times are in a range of about 20 s to about 7 min or about 30 s to about 6 min at room temperature (23° C.). For impression materials oral setting times should be as short as possible. Suitable oral setting times are ≦about 6 min or ≦about 5 min.

The invention is hereinafter described by examples. The examples are not intended to limit the scope of the invention.

Materials

Prepolymers:

| Designation | mole ratio EO:THF | Mol. weight, $M_n$ | End-group |
|---|---|---|---|
| Prepolymer A | ≈1:4 | ca. 6000 | carbonyl imidazolide |
| Prepolymer B | ≈1:4 | ca. 3000 | carbonyl imidazolide |
| Prepolymer C | ≈1:4 | ca. 6000 | carbonyl benzimidazolide |

Crosslinkers:

| Designation | Molecular weight | Tradename | Source |
|---|---|---|---|
| XL A | 600 ($M_n$) | LUPASOL FG Polyethylenimine | BASF AG (Ludwigshafen, Germany) |
| XL B | 250-300 ($M_n$) | ETHYLENEAMINE E-100 | Huntsman Corp. (Houston, TX, USA |
| XL C | 1300 ($M_n$) | LUPASOL G20 Waterfree Polyethylenimine | BASF AG (Ludwigshafen, Germany) |
| XL D | 423 ($M_n$) | Polyethylenenimine (mixture of branched and linear) | Aldrich Chemical Co. Inc. (Milwaukee, WI, USA) |

Crosslinker A—"XL A"—LUPASOL FG Polyethylenimine (available commercially from BASF AG, Ludwigshafen, Germany) is a low molecular weight ethylene imine polymer. Mw ca. 800 as determined by light scattering, Mn ca. 600 as determined by gel permeation chromatography (CAS # 25987-06-8).

Crosslinker B—"XL B"—Ethyleneamine E-100 (CAS #00068131-73-7) (available commercially from Huntsman Corp., Houston, Tex., USA ) is a mixture of tetraethylenepentamine (TEPA), pentaethylenehexamine (PEHA), hexaethyleneheptamine (HEHA), and higher molecular weight products. E-100 is a complex mixture of various linear, cyclic, and branched products with a number-average molecular weight of 250-300 g/mole.

Crosslinker C—"XL C"—LUPASOL G20 Waterfree Polyethylenimine (available commercially from BASF AG, Ludwigshafen, Germany) is a low molecular weight ethylenimine polymer. Average molecular weight: 1,300 (CAS # 25987-06-8).

Crosslinker D—"XL D"—polyethyleneimine H(—NHCH$_2$—CH$_2$—NH—)nH (mixture of linear and branched chains) CAS # 29320-38-5 number avereage molecular weight, $M_n$=423 (Aldrich Chemical Co. Inc. # 468533).

Test Methods

Molecular Weight ($M_n$) of the Prepolymer:

Proton ($^1$H) NMR techniques were employed to estimate the molecular weight of the polyol precursor of the prepolymer. Integrated signals of the terminal —CH$_2$— groups were compared to the integrated sum of proton signals from backbone hydrocarbon protons taking into account co-monomer ratio, if applicable. To achieve appropriate separation of terminal methylene proton signals from the backbone proton signals, terminal hydroxyl groups were esterified with trifluoroacetic acid.

Curing Time of the Curable Composition:

The curing time for the curable compositions of the examples was measured by 1) mixing the prepolymer and crosslinker components with a spatula on a mixing pad for about 30 seconds and 2) placing a sample of the mixture having a weight of ca. 2 g onto the specimen platform of a Strawbury Curometer (H. W. Wallace and Co., Ltd., Croydon, UK).

The device moved a stylus back and forth in the mixture and recorded the degree of movement graphically. A high degree of freedom of movement indicated a low viscosity. Thus when the viscosity of the curable composition began to change as visually reflected in the reduced movement of the recorder pen, that point was taken as the time of cure start or T1. When the stylus could no long move and no further change in viscosity could be detected, the curing was judged to be complete and that time was taken as T2. The curing time was calculated as the difference between T2 and T1. Approximate curing time in minutes was recorded.

Tensile Strength (MPa) and Elongation at Break (%)

Tensile strength and Elongation at break were measure according to Deutsche Industrie Norm (DIN) or European Norm (EN) Method # 53504 (geometry S2, 200 mm/min) using Universalprufmaschine Zwick Z020 (Zwick GmbH & Co, Ulm, Germany).

Shore A Hardness (After 24 Hours)

Shore A hardness was measured according to Deutsche Industrie Norm (DIN) Method # 53505. The curable compositions were allowed to cure for 24 hours at 23° C. and ambient humidity before the hardness was measured.

EXAMPLE 1

A polyether diol, prepared by the polymerization of tetrahydrofuran and ethylene oxide in a mole ratio of 4:1 (having a molecular weight of 6440 g/mole as measured by $^1$H NMR according to the method given above under TEST METHODS), was reacted with an excess of carbonyl-diimidazole (available from Aldrich Chemical Co., Milwaukee, Wis., USA) to form a linear polyether terminated on each end with a carbonyl imidazolide residue. The prepolymer had an estimated molecular weight of 6628 g/mole by calculation based on a quantitative reaction and is designated hereafter as "Prepolymer A" (cf. Example 1 of US 2004/0149164).

Polyethylene imine, obtained commercially as LUPASOL FG (BASF, Ludwigshafen, Germany), was employed as received. LUPASOL FG is a low molecular weight ethylenimine copolymer having an average molecular weight of ca. 800 and is designated hereafter as "XL A".

A prepolymer (imidazolide-capped polyether "Prepolymer A" (1.50 g)) and a polyethylene imine crosslinker ("XL A" (0.039 g) ) were combined in a polymeric screw cap bottle and mixed using a centrifugal mixer commercially available as SPEEDMIXER MODEL DAC 150 FVZ centrifugal mixer from Hausschild Engineering GmbH (Hamm, Germany). The capsule was spun at 3,000 rpm for a period of 30 seconds to effect mixing.

The equivalent ratio of components (activated prepolymer: crosslinker) was 1:0.5 *.

* For XL-A, XL-B and XL-C only

* The equivalent ration was calculated in the following manner: Polyethyleneimines (PEIs) like XL-A, XL-B, XL-C or XL-D, which can be produced by polymerising aziridine, are known to comprise a mixture of molecules containing tertiary, secondary and primary amines in the statistical ratio of approximately 1:2:1 (Encyclopedia of Polymer Sciences and Engeneering (Ed. H. Mark et al) Volume 1, Chapter: Alkylenelimine Polymers, pp. 688-695, A Wiley-Interscience Publication, New York, 1985). Primary amines react quickly with the imidazolide-capped polyethers. If primary amine groups are present only, the primary amine groups are considered to be reactive.

Thus, four times the equivalent weight of aziridine (43 g/mole) or 172 g/mole must be taken for each equivalent of imidazolide-capped polyether to give a stoichiometric ratio of 1:1 (primary amine groups:imidazolide groups). This ratio of equivalents of imidazolide groups of the activated prepolymer to amine content of the crosslinker would be called 1:1 according to the system employed herein.

The curing time was measured according to the method given above under TEST METHODS. The chemical composition of the curable composition of Example 1 is summarized in Table 1.

Properties of the cured composition, including tensile strength, elongation at break and Shore A hardness, were measured according to the methods shown under TEST METHODS above and are summarized in Table 2.

EXAMPLES 2-6

Examples 2-6 were prepared by essentially the same method as Example 1 with the exception that the ratio of the polyether ("Prepolymer A") and polyethyleneimine ("XL A") components was varied. Chemical compositions of Examples 2-6 are summarized in Table 1. The curing times and physical properties of the cured compositions are summarized in Table 2.

EXAMPLE 7-9

Compositions were prepared using the procedure of Examples 1-6, with the exception that "Prepolymer A" was reacted with polyethylene imine crosslinkers having molecular weights higher and lower, respectively, as compared to "XL A" of Examples 1-6. These include:

"XL B" (Ethyleneamine E-100 (CAS # 00068131-73-7) available commercially from Huntsman Corp., Houston, Tex., USA ), a mixture of tetraethylenepentamine (TEPA), pentaethylenehexamine (PEHA), hexaethyleneheptamine (HEHA), and higher molecular weight products. E-100 is a complex mixture of various linear, cyclic, and branched products with a number-average molecular weight of 250-300 g/mole) and "XL C" (LUPASOL G20 Waterfree Polyethylenimine, available commercially from BASF AG, Ludwigshafen, Germany, a low molecular weight ethylenimine polymer having an average molecular weight of 1,300). Chemical compositions are summarized in Table 1.

Properties of the cured compositions are shown in Table 2.

EXAMPLES 10-11

Examples 10 and 11 were prepared using a prepolymer comprising a polyether end-capped with a benzimidazolide residue, rather than a polyether end-caped with an imidazolide residue as in previous examples.

The benzimidazolide-capped polyether "Prepolymer C" was prepared by the following procedure. A polyether diol, prepared by the polymerization of tetrahydrofuran and ethylene oxide in a mole ratio of 4:1 (having a molecular weight of 5024 g/mole as measured by $^1$H NMR according to the method given above under TEST METHODS), was reacted with an excess of carbonyl-dibenzimidazole (available from phosgene and benzimidazole) to form a linear polyether that was terminated on each end with a carbonyl imidazolide residue. The prepolymer had a molecular weight of 5314 g/mole by calculation based on a quantitative reaction.

"Prepolymer C" was used in conjunction with a polyethylene imine crosslinker (XL A) in two differing ratios to produce the compositions of Examples 10 and 11. Chemical compositions are summarized in Table 1. Properties of the cured compositions are shown in Table 2.

EXAMPLE 12

Example 12 was prepared by a procedure similar to Examples 1-6, with the exception that an prepolymer comprising imidazolide-capped polyether having a lower molecular weight was employed ("Prepolymer B").

"Prepolymer B" was prepared by the following procedure: A polyether diol was prepared by the polymerization of tetrahydrofuran and ethylene oxide in a mole ratio of 4:1 (having a molecular weight of 2662 g/mol as measured by 1H NMR according to the method given above under TEST METHODS), was reacted with an excess of carbonyl-diimidazole (available from Aldrich Chemical Co., Milwaukee, Wis., USA) to form a linear polyether terminated on each end with a carbonyl imidazolide residue. The prepolymer had a molecular weight of 2850 g/mole by calculation based on a quantitative reaction.

COMPARATIVE EXAMPLE 1

An aziridine-capped polyether was prepared according to methods described in U.S. Pat. No. 3,453,742 (cf. Ex. 13 and 40) starting from a diol having a molecular weight of ca. 6,500 (obtained by the polymerization of tetrahydrofuran and thylene oxide in a mole ration of 1:1).

The aziridine-capped polyether thus obtained was then crosslinked by means of acid-catalyzed, ring-opening cationic polymerization. Aziridine-capped polyether (1.5 g) was mixed with 0.3 g of a catalyst solution comprising 41.5% by weight sulfonium salt having a molecular weight of 385 g/mol in acetyl tributyrocitrate to effect crosslinking.

The polyether-based composition that resulted was tested by the same methods as the materials of the invention. Properties of the cured composition are summarized in Table 2.

TABLE 1

| | Prepolymer | | | Crosslinker | | | |
|---|---|---|---|---|---|---|---|
| Ex. | Type | Mol. wt, Mw | Weight, g | Type | Mol. wt, Mw | Weight, g | Equiv. ratio* |
| 1 | Prepolymer A | 6628 | 1.5 | XL A | 800 | 0.039 | 1.00:0.50 |
| 2 | Prepolymer A | 6628 | 1.5 | XL A | 800 | 0.058 | 1.00:0.75 |
| 3 | Prepolymer A | 6628 | 1.5 | XL A | 800 | 0.078 | 1.00:1.00 |
| 4 | Prepolymer A | 6628 | 1.5 | XL A | 800 | 0.098 | 1.00:1.25 |
| 5 | Prepolymer A | 6628 | 1.5 | XL A | 800 | 0.117 | 1.00:1.50 |
| 6 | Prepolymer A | 6628 | 1.5 | XL A | 800 | 0.156 | 1.00:2.00 |
| 7 | Prepolymer A | 6628 | 1.5 | XL B | 270 | 0.053 | 1.00:0.60 |
| 8 | Prepolymer A | 6628 | 1.5 | XL C | 1300 | 0.078 | 1.00:1.00 |
| 9 | Prepolymer A | 6628 | 1.5 | XL C | 1300 | 0.156 | 1.00:2.00 |
| 10 | Prepolymer C | 5314 | 1.5 | XL A | 800 | 0.097 | 1.00:1.00 |
| 11 | Prepolymer C | 5314 | 1.5 | XL A | 800 | 0.147 | 1.00:1.50 |
| 12 | Prepolymer B | 2850 | 1.5 | XL A | 800 | 0.181 | 1.00:1.00 |

*Ratio of equivalents imidazolide group of prepolymer to equivalents of primary amine in crosslinker

TABLE 2

Properties of Cured Compositions

| Example | Tensile strength (MPa) | Elongation at break (%) | Shore A hardness | Curing time, min |
|---|---|---|---|---|
| 1 | 1.29 | 278 | 42 | 16 |
| 2 | 1.79 | 212 | 52 | 9 |
| 3 | 2.08 | 392 | 48 | 6 |
| 4 | 1.98 | 497 | 42 | 4 |
| 5 | 1.93 | 684 | 35 | 3 |
| 6 | 1.30 | 1036 | 18 | 3 |
| 7 | 3.60 | 1368 | * | * |
| 8 | 1.53 | 130 | 54 | * |
| 9 | 1.53 | 220 | 45 | 4 |
| 10 | 2.00 | 342 | 46 | 15 |
| 11 | 1.63 | 716 | 29 | 12 |
| 12 | 1.27 | 110 | 50 | 2 |
| Comp. Ex. 1 | 1.18 | 57 | 60 | 3 |

* = not measured

EXAMPLES 13-15

Examples 13-15 were prepared by reacting "Prepolymer A" (Mn 6,000, polyether capped with imidazolide end groups) with a crosslinker comprising a linear polyethlene imine ("XL D") in the ratios summarized in Table 3. "XL D" is predominately linear polyethyleneimine having a molecular weight of 423 (Aldrich Chemical Co. Inc., Milwaukee, Wis., USA).

Properties of the resulting cured compositions are shown in Table 4.

TABLE 3

Compositions with crosslinker XL D

| | Prepolymer | | | Crosslinker | | | |
|---|---|---|---|---|---|---|---|
| Ex. | Type | Mol. wt, $M_w$ | Weight, g | Type | Mol. wt, $M_w$ | Weight, g | Equiv. ratio** |
| 13 | Prepolymer A | 6418 | 1.5 | XL D | 423 | 0.030 | 1.00:1.50 |
| 14 | Prepolymer A | 6418 | 1.5 | XL D | 423 | 0.053 | 1.00:2.50 |
| 15 | Prepolymer A | 6418 | 1.5 | XL D | 423 | 0.060 | 1.00:3.00 |

**ratio of equivalents of imidazolide group of prepolymer to equivalents of amine in crosslinker

TABLE 4

Properties of Cured Compositions with Crosslinker XL D

| Example | Tensile strength (MPa) | Elongation at break (%) | Shore A hardness | Curing time, minutes |
|---|---|---|---|---|
| 13 | 2.19 | >2000 | * | * |
| 14 | 3.05 | 1299 | 37 | * |
| 15 | 1.92 | 1775 | * | * |

* Not measured

The invention claimed is:

1. A method for producing a cured composition comprising the steps of:
providing a first component comprising an activated prepolymer (A) having the formula:

(L-C(=O)-O-)$_n$P wherein
L is a group represented by the following formula

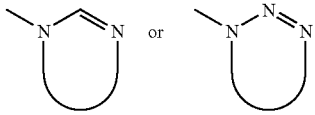

with the N,N' bridging unit being part of a heterocyclic quasi-aromatic ringsystem, optionally containing O, N or S,
P is a prepolymer backbone having a molecular weight (Mn) of at least 500,
n is at least 2;
providing a second component comprising a crosslinker (B) comprising at least 3 nucleophilic groups,
mixing the first component and the second component to form a curable composition; and
curing the curable composition, wherein curing is affected at a temperature below 50° C. within 1 hour.

2. The method according to claim 1, wherein the composition is a dental material.

3. The method according to claim 2, wherein the dental material is an impression material, bite registration material, duplicating material or modelling material.

4. The method according to claim 1, wherein the composition after curing has a tensile strength above 0.3 MPa and up to 6 MPa.

5. The method according to claim 1, wherein one or both of the first and second components further comprises at least one filler (C) and at least one additive (D).

6. The method according to claim 5, wherein the additive (D) is selected from the group consisting of network modifiers, dyes, pigments, thixotropic agents, flow improvers, polymeric thickeners, surfactants, odorous substances, diluters, and flavourings.

7. The method according to claim 1, wherein L is selected from the group consisting of substituted or unsubstituted imidazole, triazole, pyrazole triazole, tetrazole, benzimidazole, and benzotriazole, wherein substituents for the substituted groups comprise $C_1$ to $C_6$ alkyl or aryl groups.

8. The method according to claim 1, wherein the prepolymer (A) has a linear, branched, hyperbranched, block polymeric, multi-block polymeric, random polymeric, gradient polymeric, alternating co- and ter-polymeric, or dendrimeric structure.

9. The method according to claim 1, wherein the prepolymer backbone P comprises structural units selected from the group consisting of polyethylene-glycol, polypropylene-glycol, polypropylene-diol, polypropylene-triol, polytetrahydrofurane, polycaprolactone-diol, polycaprolactone-triol, and polyglycerol.

10. The method according to claim 1, wherein the nucleophilic groups of crosslinker (B) contain at least one N, O or S.

11. The method according to claim 1, wherein the nucleophilic groups of crosslinker (B) comprise —$NH_2$ groups.

12. The method according to claim 1, wherein the crosslinker (B) has a molecular weight ($M_n$) of at least 400.

13. The method according to claim 1, wherein crosslinker (B) is selected from the group consisting of polyethyleneimine, polyallylamine, tris-aminoethyl-amine, polypropylenimin-tetramin, polyamidoamine, and polyglucosamine.

14. The method according to claim 1, the composition characterized by at least one of the following parameters after curing: a tensile strength of at least 0.8 MPa after 24 h, a elongation at break of at least 40% after 24 h, and/or a shore A hardness after 24 h, of at least 23.

15. The method according to claim 1, wherein the curable composition comprises:
a prepolymer (A) at an amount of about 10 to about 80 wt.-%,
a crosslinker (B) at an amount of about 0.1 to about 20 wt.-%,
a filler (C) at an amount of about 0 to about 80 wt.-%, and
a additive (D) at an amount of 0 to about 50 wt.-%.

16. The method according to claim 1, wherein the mixing ratio of the first component and the second component is in the range of about 0.5:1 to about 15:1.

17. The method according to claim 1, wherein the mixing is carried out manually or automatically using a static or dynamic mixing device.

18. A method for taking a dental impression, the method comprising the steps of:
providing a curable composition comprising:
(a) at least one prepolymer (A) having the formula:

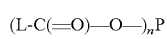

wherein
L is a group represented by the following formula

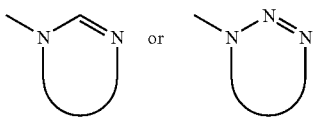

with the N,N' bridging unit being part of a heterocyclic quasi-aromatic ringsystem, optionally containing O, N or S,
P is a prepolymer backbone having a molecular weight (Mn) of at least 500,
n is at least 2; and
(b) at least one crosslinker (B) comprising at least 3 nucleophilic groups;
contacting the curable composition with the tooth of a patient; and
allowing the composition to cure.

19. A method for making a dental product, the method comprising the steps of:
providing a curable composition comprising:
(a) at least one prepolymer (A) having the formula:

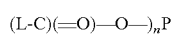

wherein
L is a group represented by the following formula

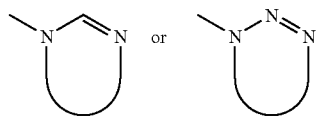

with the N,N' bridging unit being part of a heterocyclic quasi-aromatic ringsystem, optionally containing O, N or S,
P is a prepolymer backbone having a molecular weight (Mn) of at least 500,
n is at least 2 and
(b) at least one crosslinker (B) comprising at least 3 nucleophilic groups;
contacting the curable composition with the tooth of a patient;
allowing the composition to cure to form a cured composition; and
using the cured composition in a duplicating or modelling process to form a dental product.

20. The method according to claim 19, wherein the dental product is an inlay, onlay, crown, or bridge.

21. The method according to claim 18, wherein the composition after curing has a tensile strength above 0.3 MPa and up to 6 MPa.

22. The method according to claim 18, wherein the curable composition further comprises at least one filler (C) and at least one additive (D).

23. The method according to claim 22, wherein the additive (D) is selected from the group consisting of network modifiers, dyes, pigments, thixotropic agents, flow improvers, polymeric thickeners, surfactants, odorous substances, diluters, and flavourings.

24. The method according to claim 18, wherein L is selected from the group consisting of substituted or unsubstituted imidazole, triazole, pyrazole triazole, tetrazole, benzimidazole, and benzotriazole, wherein substituents for the substituted groups comprise $C_1$ to $C_6$ alkyl or aryl groups.

25. The method according to claim 18, wherein the prepolymer (A) has a linear, branched, hyperbranched, block polymeric, multi-block polymeric, random polymeric, gradient polymeric, alternating co- and ter-polymeric, or dendrimeric structure.

26. The method according to claim 18, wherein the prepolymer backbone P comprises structural units selected from the group consisting of polyethylene-glycol, polypropyleneglycol, polypropylene-diol, polypropylene-triol, polytetrahydrofurane, polycaprolactone-diol, polycaprolactone-triol, and polyglycerol.

27. The method according to claim 18, wherein the nucleophilic groups of crosslinker (B) contain at least one N, O or S.

28. The method according to claim 18, wherein the nucleophilic groups of crosslinker (B) comprise —$NH_2$ groups.

29. The method according to claim 18, wherein the crosslinker (B) has a molecular weight ($M_n$) of at least 400.

30. The method according to claim 18, wherein crosslinker (B) is selected from the group consisting of polyethyleneimine, polyallylamine, tris-aminoethyl-amine, polypropylenimin-tetramin, polyamidoamine, and polyglucosamine.

31. The method according to claim 18, the composition characterized by at least one of the following parameters after curing: a tensile strength of at least 0.8 MPa after 24 h, a elongation at break of at least 40% after 24 h, and/or a shore A hardness after 24 h, of at least 23.

32. The method according to claim 18, wherein the curable composition comprises:
 a prepolymer (A) at an amount of about 10 to about 80 wt.-%,
 a crosslinker (B) at an amount of about 0.1 to about 20 wt.-%,
 a filler (C) at an amount of about 0 to about 80 wt.-%, and
 a additive (D) at an amount of 0 to about 50 wt.-%.

* * * * *

UNITED STATES PATENT AND TRADEMARK OFFICE
CERTIFICATE OF CORRECTION

PATENT NO. : 7,700,666 B2
APPLICATION NO. : 11/423021
DATED : April 20, 2010
INVENTOR(S) : Peter Bissinger et al.

It is certified that error appears in the above-identified patent and that said Letters Patent is hereby corrected as shown below:

Column 2
Line 37, delete "ringsytem" and insert -- ringsystem --, therefor.
Line 43, delete "bezimidazole," and insert -- benzimidazole, --, therefor.

Column 3
Line 41, delete "Encylopedia" and insert -- Encyclopedia --, therefor.

Column 8
Line 39, delete "liqids" and insert -- liquids --, therefor.

Column 11
Line 40, delete "avereage" and insert -- average --, therefor.
Line 60, delete "Strawbury" and insert -- Strawberry --, therefor.

Column 12
Line 49, delete "ration" and insert -- ratio --, therefor.

Column 14
Line 38, delete "thylene" and insert -- ethylene --, therefor.
Line 38, delete "ration" and insert -- ratio --, therefor.

Column 15
Lines 27-28, delete "polyethlene" and insert -- polyethylene --, therefor.

Column 16
Line 62, In claim 8, delete "ter-polymeric," and insert -- terpolymeric, --, therefor.

Column 17
Lines 1-2, In claim 9, delete "polytetrahydrofurane," and insert -- polytetrahydrofuran, --, therefor.

Signed and Sealed this
Twenty-eighth Day of December, 2010

David J. Kappos
*Director of the United States Patent and Trademark Office*

Column 18
Line 16, In claim 19, after "2" insert -- ; --.
Line 47, In claim 25, delete "ter-polymeric," and insert -- terpolymeric, --, therefor.
Lines 47-48, In claim 26, delete "polytetrahydrofurane," and insert -- polytetrahydrofuran, --, therefor.